(12) United States Patent
Hsieh

(10) Patent No.: US 11,528,983 B1
(45) Date of Patent: Dec. 20, 2022

(54) MULTIFUNCTIONAL PILL BOX CARRYING POUCH

(71) Applicant: Ming-Jen Hsieh, Taipei (TW)

(72) Inventor: Ming-Jen Hsieh, Taipei (TW)

( * ) Notice: Subject to any disclaimer, the term of this patent is extended or adjusted under 35 U.S.C. 154(b) by 0 days.

(21) Appl. No.: 17/357,036

(22) Filed: Jun. 24, 2021

(51) Int. Cl.
| | |
|---|---|
| A61J 1/03 | (2006.01) |
| A45F 3/00 | (2006.01) |
| A45F 4/00 | (2006.01) |
| A45F 3/14 | (2006.01) |
| A61B 17/132 | (2006.01) |
| A61F 5/058 | (2006.01) |
| A61F 17/00 | (2006.01) |
| A61B 17/12 | (2006.01) |

(52) U.S. Cl.
CPC .......... *A45F 3/14* (2013.01); *A45F 3/005* (2013.01); *A45F 4/00* (2013.01); *A61B 17/1325* (2013.01); *A61F 5/05825* (2013.01); *A61F 5/05841* (2013.01); *A61F 17/00* (2013.01); *A61J 1/03* (2013.01); *A45F 2003/003* (2013.01); *A45F 2003/006* (2013.01); *A45F 2200/0516* (2013.01); *A45F 2200/0583* (2013.01); *A61B 2017/12004* (2013.01)

(58) Field of Classification Search
CPC .......... A45F 3/005; A45F 2003/006; A45F 2005/008; A45F 4/02; A61J 1/03
USPC .......... 224/219, 221, 222, 267, 579
See application file for complete search history.

(56) References Cited

U.S. PATENT DOCUMENTS

| | | | | |
|---|---|---|---|---|
| 3,130,883 | A * | 4/1964 | Mackool | A45F 5/14 224/684 |
| 3,199,754 | A * | 8/1965 | Sorensen | B60N 3/12 224/222 |
| D249,592 | S * | 9/1978 | Libonati | D3/226 |
| 4,515,300 | A * | 5/1985 | Cohen | A45F 3/04 224/579 |
| D288,743 | S * | 3/1987 | Taylor | D3/226 |
| 5,129,560 | A * | 7/1992 | Herman | A45F 3/00 224/582 |
| 5,318,084 | A * | 6/1994 | Jackson | A45C 13/30 224/264 |
| 5,345,633 | A * | 9/1994 | Harnish | B60N 2/879 5/639 |
| D362,540 | S * | 9/1995 | McNamara | D3/226 |

(Continued)

FOREIGN PATENT DOCUMENTS

DE 202016006658 U1 * 8/2017

*Primary Examiner* — Justin M Larson
(74) *Attorney, Agent, or Firm* — Muncy, Geissler, Olds & Lowe, P.C.

(57) ABSTRACT

A multifunctional pill box carrying pouch is revealed. The pill box carrying pouch includes at least one pill box, at least one pouch, and at least two long ties. The pill box is a rigid rectangular box while the two long ties form a single longer tie. The respective long ties are detachably connected to the pouch by the two second connecting members. The pill box carrying pouch has a limb-carrying mode and a waist-carrying mode. Users can select the limb-carrying mode of the pill box carrying pouch when user's limb is injured and a support for the limb is required. By the two long ties arranged adjacent to each other and tightened around an arm or a leg of the human body, the pill box carrying pouch is closely attached to the wound on the limb for supporting wounded area or for hemostasis.

9 Claims, 22 Drawing Sheets

(56) References Cited

U.S. PATENT DOCUMENTS

| | | | | |
|---|---|---|---|---|
| 5,586,706 | A * | 12/1996 | Ritzenhein | A45F 3/00 224/587 |
| 5,779,122 | A * | 7/1998 | Martinelli | A45F 5/02 224/236 |
| D408,134 | S * | 4/1999 | Hartmann | D3/218 |
| 5,915,558 | A * | 6/1999 | Girvetz | A61J 7/0481 368/10 |
| 6,015,064 | A * | 1/2000 | Liu | A45C 13/02 220/524 |
| D447,864 | S * | 9/2001 | Casparian | D3/218 |
| D474,594 | S * | 5/2003 | Casparian | D3/218 |
| 6,869,219 | B1 * | 3/2005 | Sala | A45C 13/30 383/117 |
| 7,124,921 | B1 * | 10/2006 | Hubbell | A45F 3/16 224/652 |
| 7,854,317 | B1 * | 12/2010 | Hebert | A45C 11/008 206/823 |
| D642,792 | S * | 8/2011 | Tremblay | D3/218 |
| 8,985,421 | B2 * | 3/2015 | Barbier | A45C 11/00 224/660 |
| D796,183 | S * | 9/2017 | Zhou | D3/203.1 |
| 9,820,558 | B1 * | 11/2017 | de Geus | F41H 1/02 |
| D861,331 | S * | 10/2019 | Appiah | D3/218 |
| D901,892 | S * | 11/2020 | Forbes | D3/215 |
| 2004/0031830 | A1 * | 2/2004 | Davis | A45C 1/04 224/222 |
| 2004/0065708 | A1 * | 4/2004 | Amram | A45F 3/047 224/579 |
| 2005/0029156 | A1 * | 2/2005 | Girzaitis | A61J 7/04 206/534 |
| 2006/0011687 | A1 * | 1/2006 | Wadley | A45F 3/00 224/587 |
| 2008/0173682 | A1 * | 7/2008 | Dvorak | A45F 3/04 224/267 |
| 2009/0050513 | A1 * | 2/2009 | Zelek | A01K 13/003 206/534 |
| 2010/0059561 | A1 * | 3/2010 | Ellis | G16H 20/30 224/267 |
| 2013/0037428 | A1 * | 2/2013 | Wingate, III | A61J 1/03 206/223 |
| 2013/0240581 | A1 * | 9/2013 | Cooper | A45F 5/00 224/222 |
| 2015/0150361 | A1 * | 6/2015 | Barbier | A45C 11/008 224/222 |
| 2017/0197756 | A1 * | 7/2017 | Stephens | B65D 1/04 |
| 2019/0223580 | A1 * | 7/2019 | Wasylko | F41C 33/041 |

* cited by examiner

MULTIFUNCTIONAL PILL BOX CARRYING POUCH

BACKGROUND OF THE INVENTION

The present invention relates to a pill box carrying device, especially to a multifunctional pill box carrying pouch mainly used outdoors.

Nowadays people (users) usually have a pill box for mounting pills they should take regularly. When they go outside, the pill box is placed into a bag to be carried with them. However, the pill box occupies a certain space in the bag with only one function. Thus the pill box available now has the shortcomings of difficulty and inconvenience of carrying around, which not only affect user's intention to carry the pill box, but also create a risk that users are unable to take medicine on time.

SUMMARY OF THE INVENTION

Therefore, it is a primary object of the present invention to provide a multifunctional pill box carrying pouch which is selected to be in a limb-carrying mode when the user's limb is injured and a support for the limb is required. By at least two long ties arranged adjacent to each other and tightened around an arm or a leg of a human body, at least one pouch with at least pill box therein is closely attached to a wound on the user's limb for providing support or hemostasis to the wound. Compared with the pill box available now being used only for mounting pills with limited function, the present pill box is more competitive in the market.

In order to achieve the above object, a multifunctional pill box carrying pouch according to the present invention includes at least one pill box, at least one pouch, and at least two long ties. The pill box is a rigid rectangular box. The pouch is composed of an opening, a mounting space, a drawstring portion, and at least two second connecting members. The opening can be closed by the drawstring portion to make the mounting space in a closed state for mounting the pill box therein. Each of the long ties is tightened around the human body and provided with a first connecting member by which the two long ties are connected to form a single longer tie. The respective long ties are detachably connected to the pouch by the at least two second connecting members. The at least two long ties are arranged adjacent to each other and tightened around an arm or a leg of the human body and then the pouch is connected to the first connecting members by the second connecting members so that the pouch is connected with the two long ties. Next the pill box is placed in the mounting space of the pouch to form a limb-carrying mode. When the two long ties form the single longer tie, the single longer tie is tightened around a waist of the human body. Then the pouch is connected to the first connecting members by the second connecting members so that the pouch is connected with the single longer tie. Next the pill box is mounted into the mounting space of the pouch to form a waist-carrying mode. When the user's limb is injured and a temporary support is required for support a wound on the limb or for hemostasis, the user can select the limb-carrying mode of the pill box pouch. By the at least two long ties arranged adjacently and tightened around the arm or the leg of the human body, the pouch with the pill box mounted therein is closely attached to the wound on the user's limb for supporting the wound or for hemostasis.

DETAILED DESCRIPTION OF THE PREFERRED EMBODIMENTS

Refer to FIGS. 1-9 and FIGS. 12-15, a multifunctional pill box carrying pouch 1 according to the present invention includes at least one pill box 30, at least one pouch 20, and at least two long ties 10.

Figure 1:
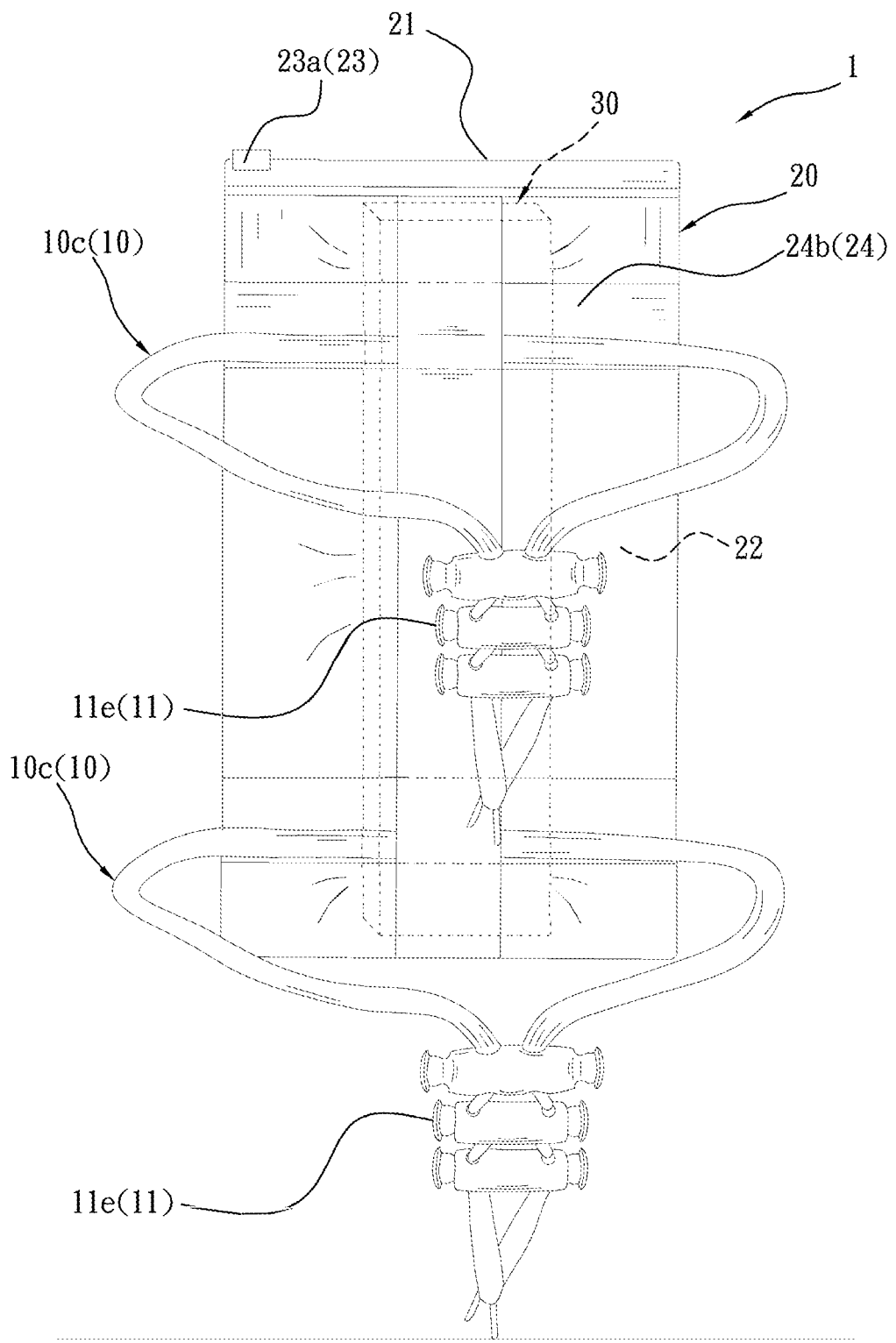
FIG. 1 is a perspective view of an embodiment in which a long tie is an elastic cord according to the present invention.
Figure 2:
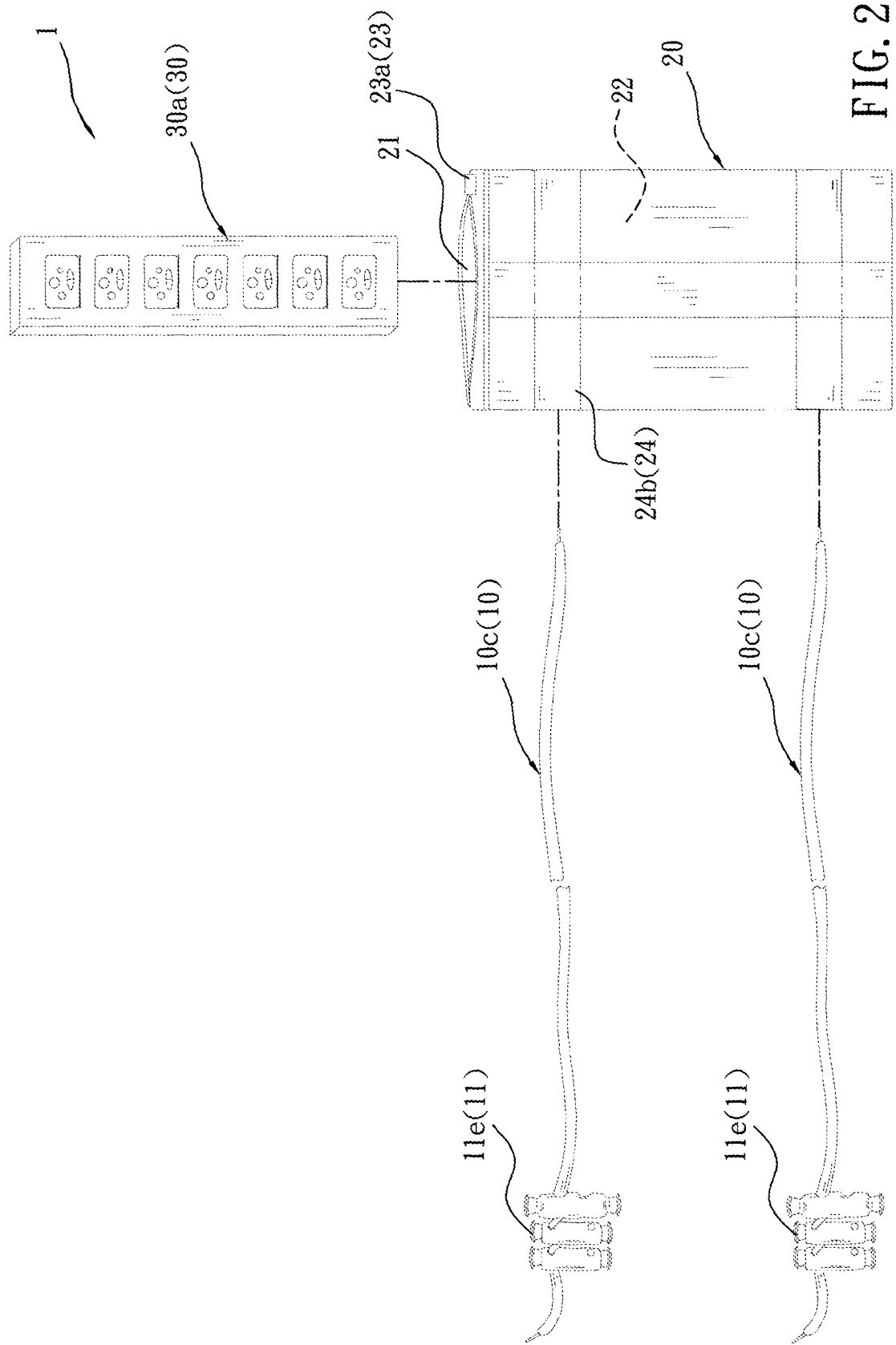
FIG. 2 is an explosive view of the embodiment in FIG. 1 according to the present invention.
Figure 3:
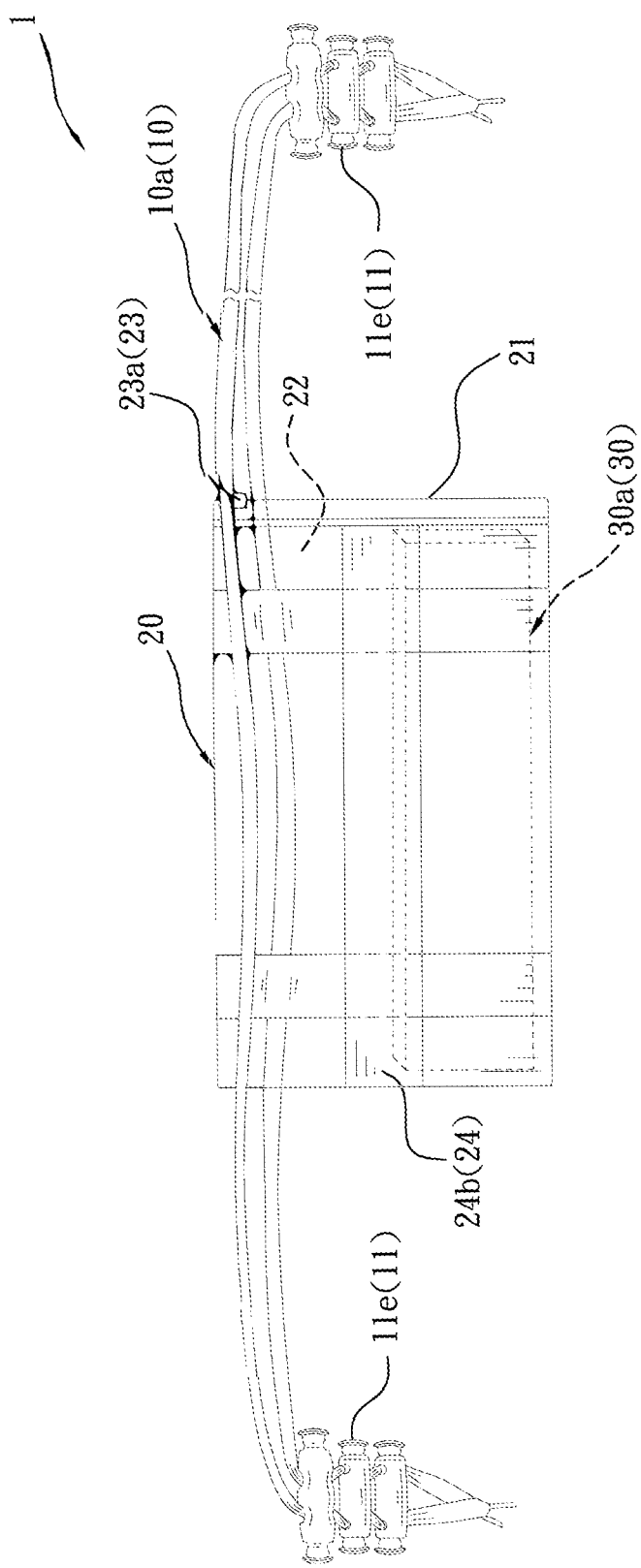
FIG. 3 is a perspective view of another embodiment in a waist-carrying mode according to the present invention.
Figure 4:
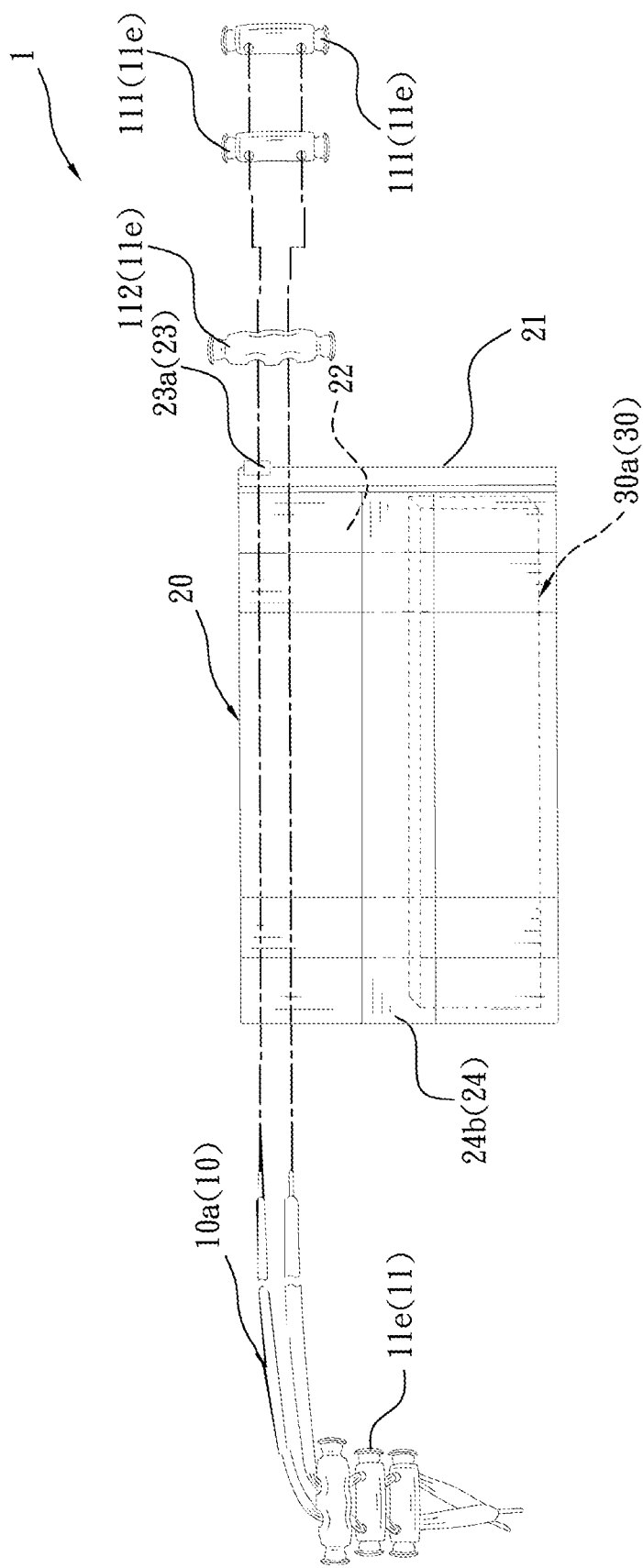
FIG. 4 is an explosive view of the embodiment in FIG. 3 according to the present invention.
Figure 5:
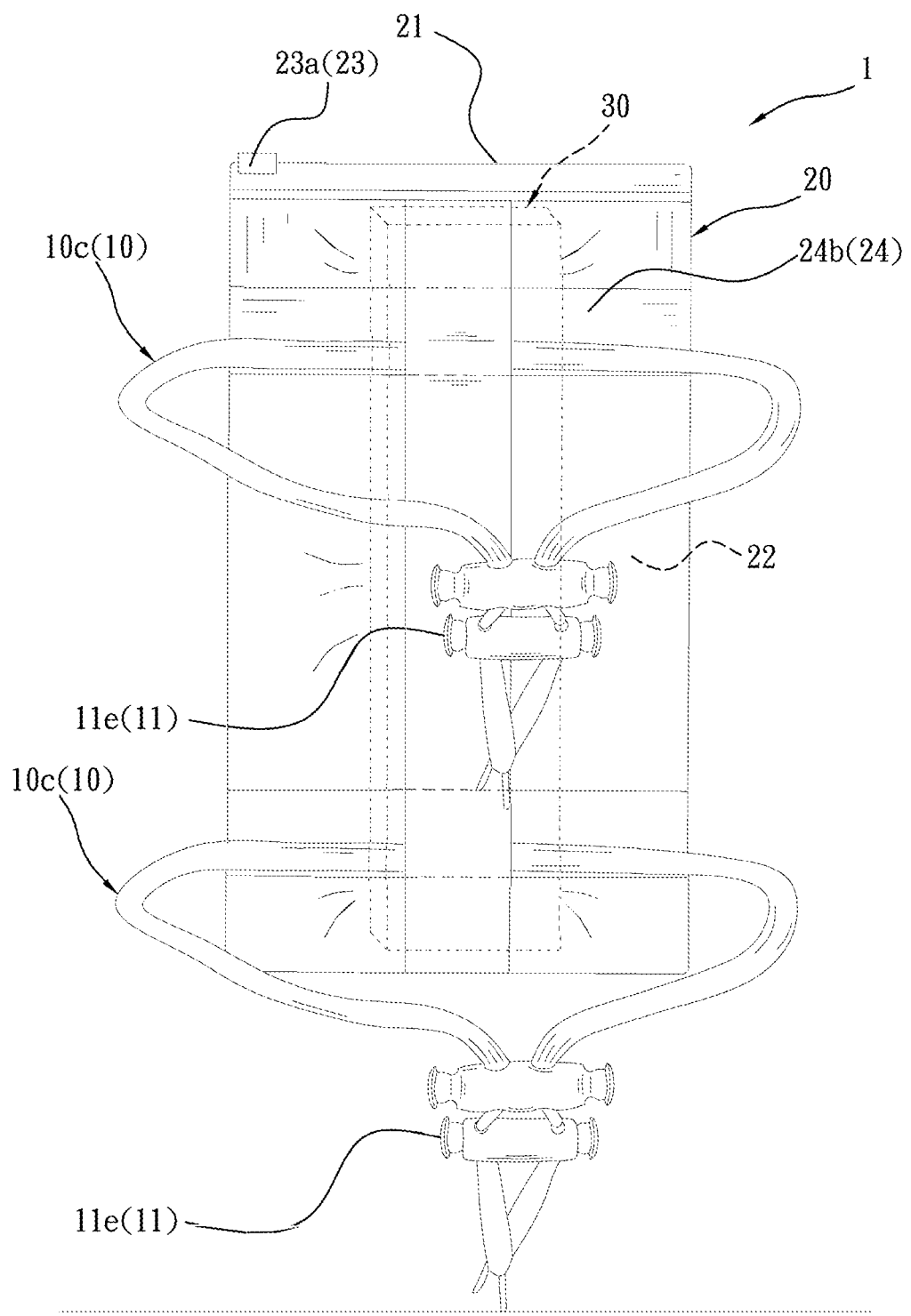
FIG. 5 is a perspective view of a further embodiment in which a first connecting member is in a form of double hole cord lock according to the present invention.
Figure 6:
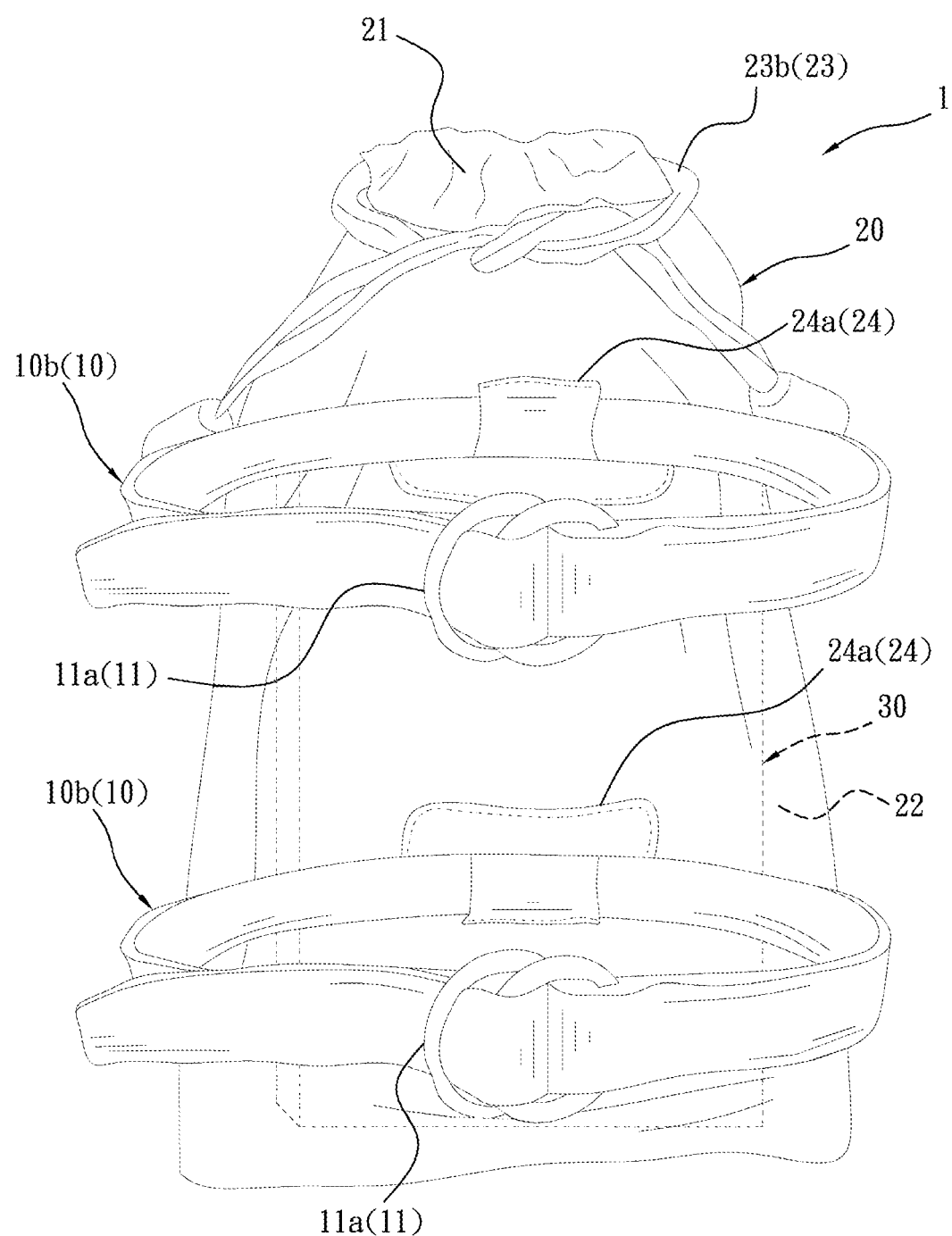
FIG. 6 is a perspective view of a further embodiment in which a long tie is a belt and a first connecting member is in a form of double buckle according to the present invention.
Figure 7:
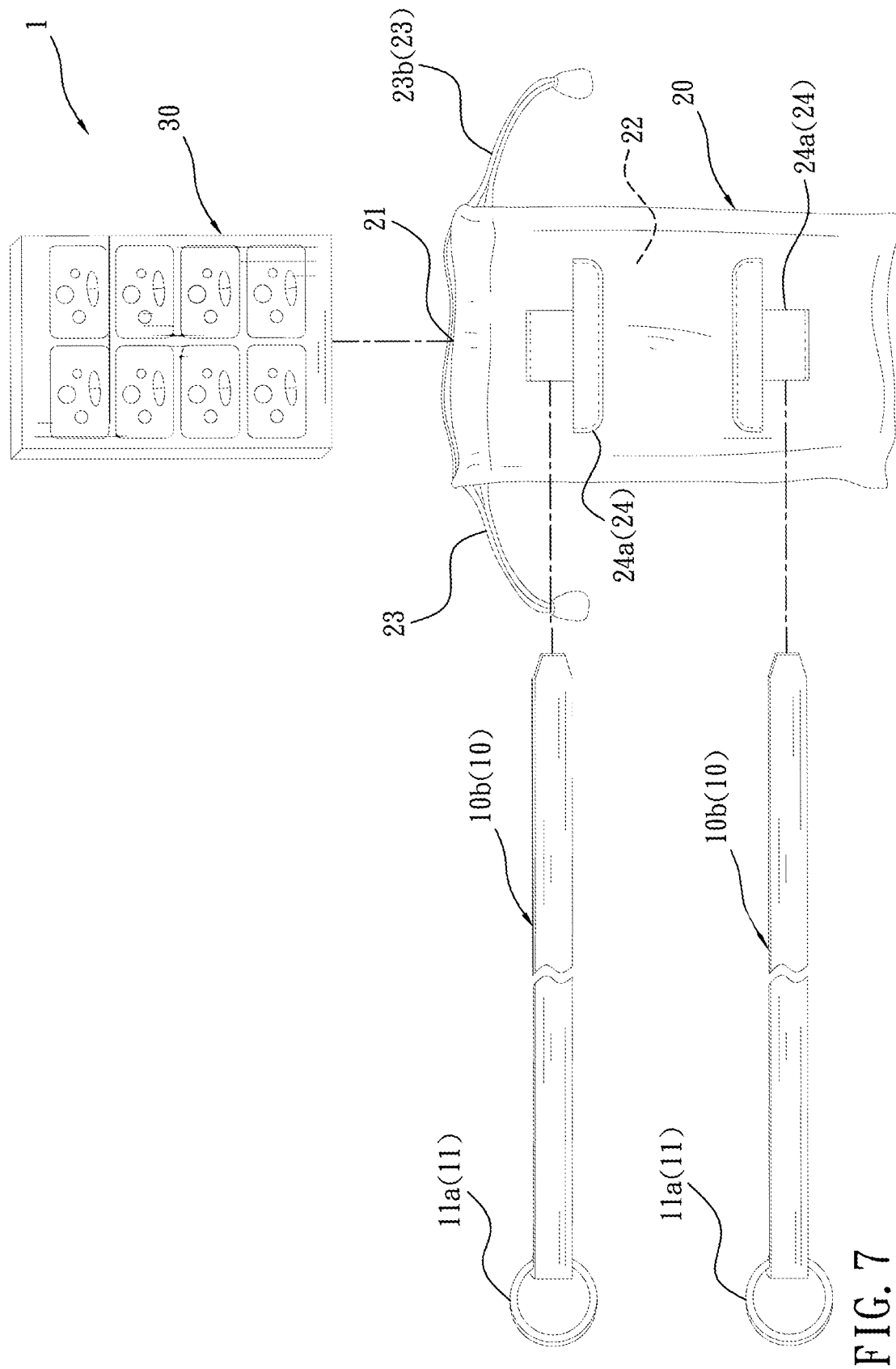
FIG. 7 is an explosive view of the embodiment in FIG. 6 according to the present invention.
Figure 8:
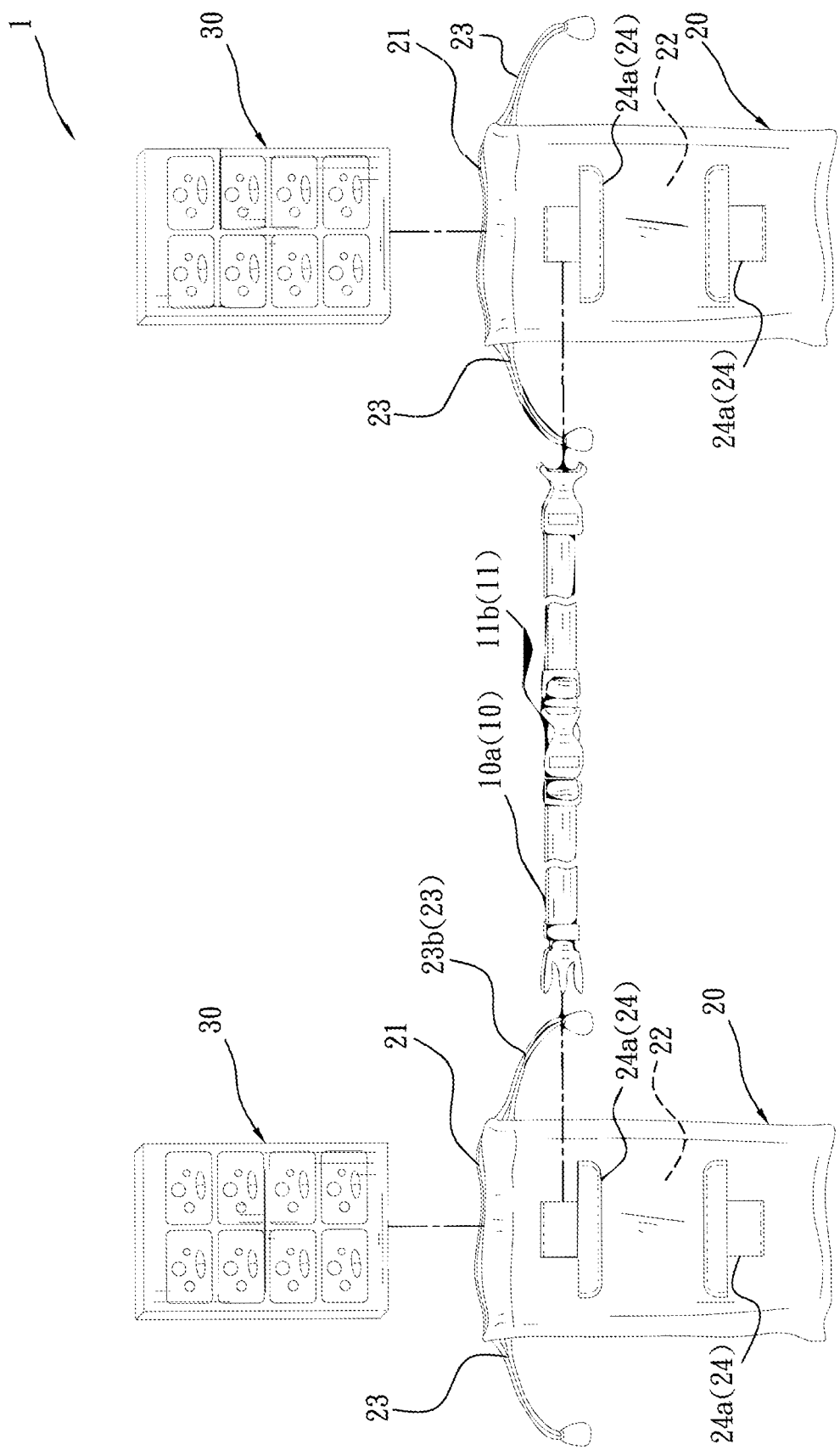
FIG. 8 is an explosive view of a further embodiment in a waist-carrying mode according to the present invention.

The pill box 30 is a rigid rectangular box which includes a main body and a cover. The main body is provided with a plurality of grids and the cover covers the main body so that each of the respective grids becomes a closed space for storage of pills. The pill box 30 can be a long strip 30a (as shown in FIG. 2) or a wide rectangle 30b (as shown in FIG. 7 and FIG. 8). The pouch 20 is made of polyethylene (PE), but not limited, and is composed of an opening 21, a mounting space 22, a drawstring portion 23, and at least two second connecting members 24. The opening 21 is able to be closed by the drawstring portion 23 so as to make the mounting space 22 in a closed state, as shown in FIG. 1 and FIG. 6. The mounting space 22 is for receiving the pill box 30, as shown in FIG. 2, FIG. 3, FIG. 6, and FIG. 7. As to the drawstring portion 23, it can be, but not limited to, a slider 23a (as shown in FIG. 1 and FIG. 2) or a drawstring 23b (as shown in FIG. 6 and FIG. 7). The second connecting member 24 can be, but not limited to, a loop type 24a (as shown in FIG. 6 and FIG. 7) or a channel type 24b (as shown in FIG. 1-3), which allows the long tie 10 to be inserted through and positioned therein quickly. Moreover, the mounting space 22 of the pouch 20 can also be used to mount other objects such as a mobile phone (not shown in figures), a water bottle (not shown in figures), or a small first aid kit (not shown in figures), but not limited, to make the present product more competitive.

As shown in FIG. 12-25, at least two long ties 10 are tightened around a human body 2. Each of the long ties 10 is provided with a first connecting member 11 by which the two long ties 10 are connected to form a single longer tie 10a, as shown in FIG. 3, FIG. 4, FIG. 8, FIG. 9, FIG. 14, and FIG. 15. The respective long ties 10 are detachably connected to the respective pouches 20 by the two second connecting members 24, as shown in FIG. 1-8.

Figure 9:
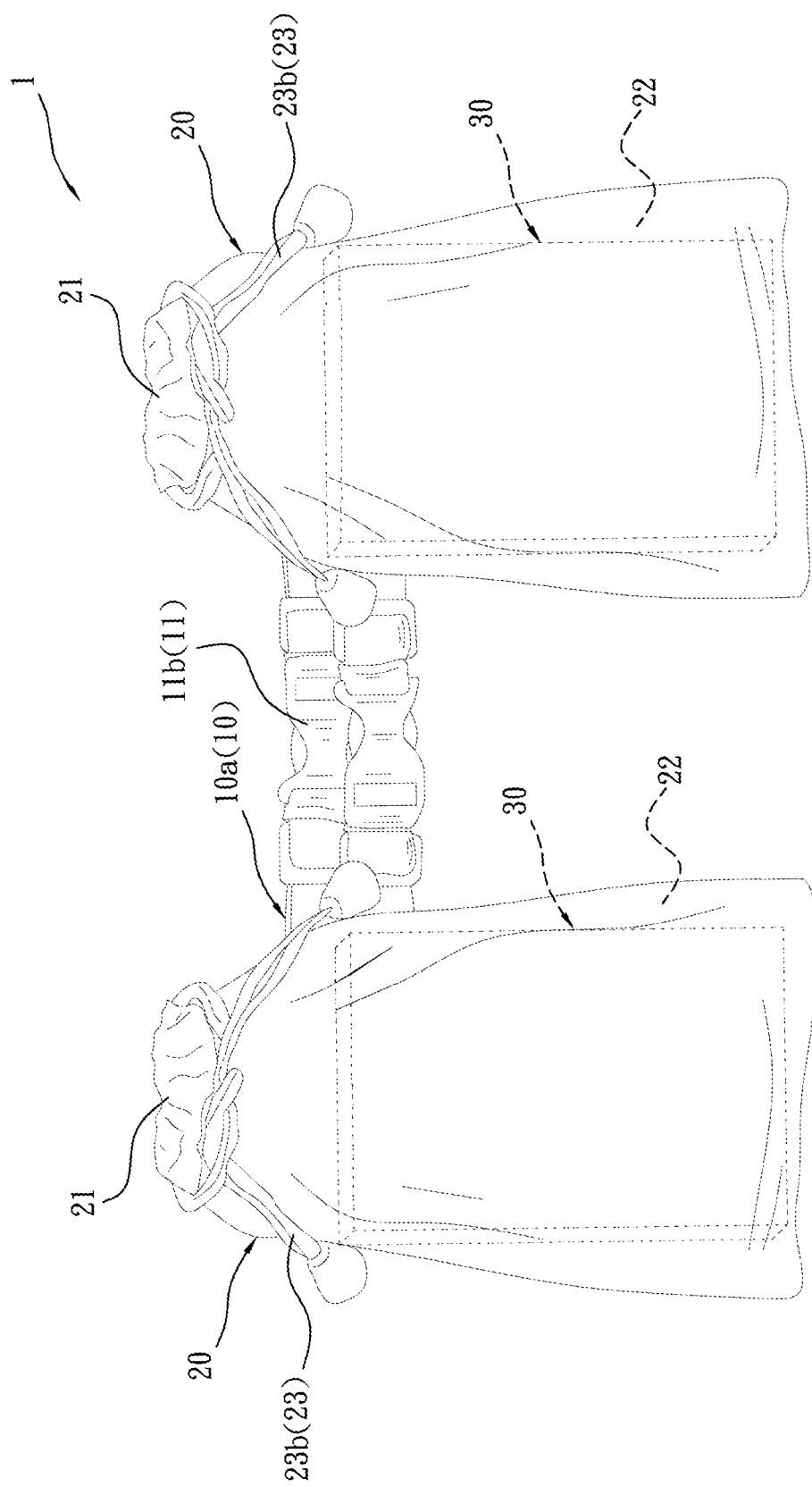
FIG. 9 is a perspective view of the embodiment in FIG. 8 according to the present invention.
Figure 10:
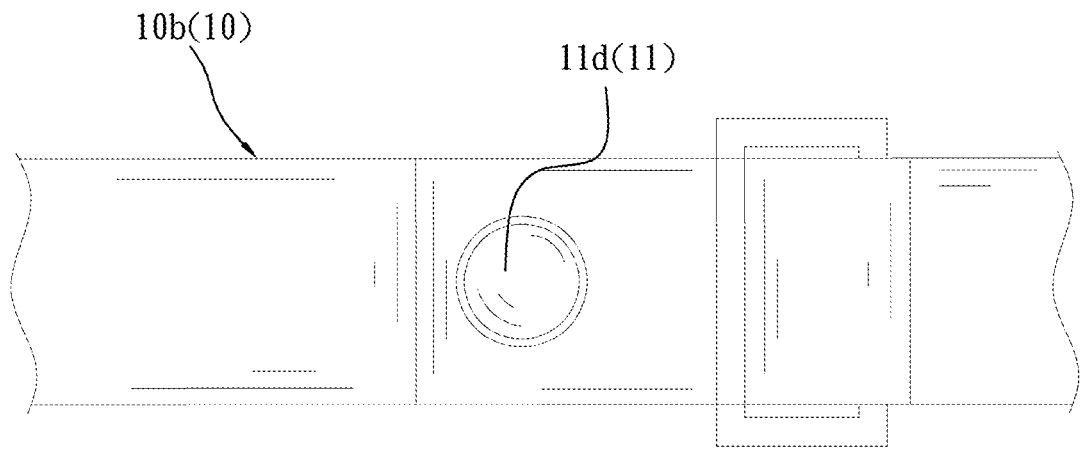
FIG. 10 is a schematic drawing showing a first connecting member which is a snap-fastener type according to the present invention.
Figure 11:
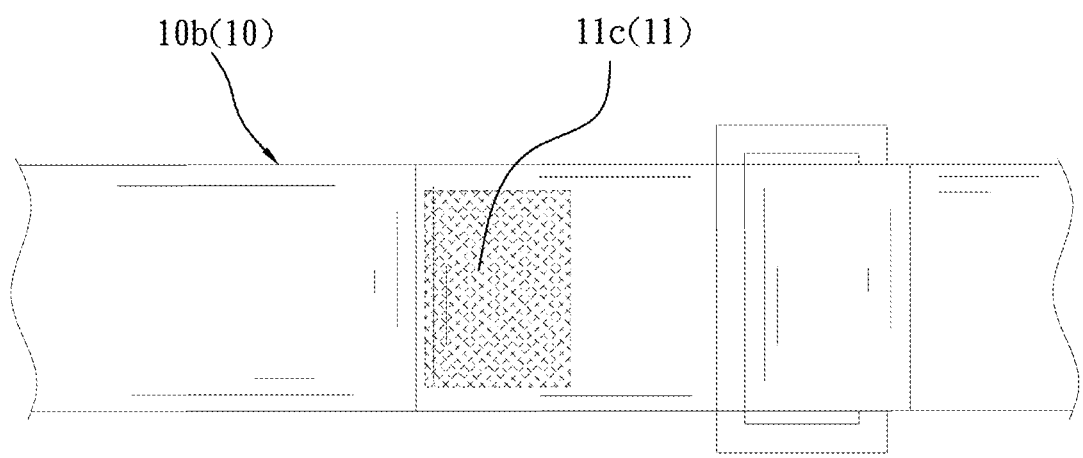
FIG. 11 is a schematic drawing showing a first connecting member which is a hook and loop type according to the present invention.
Figure 12:
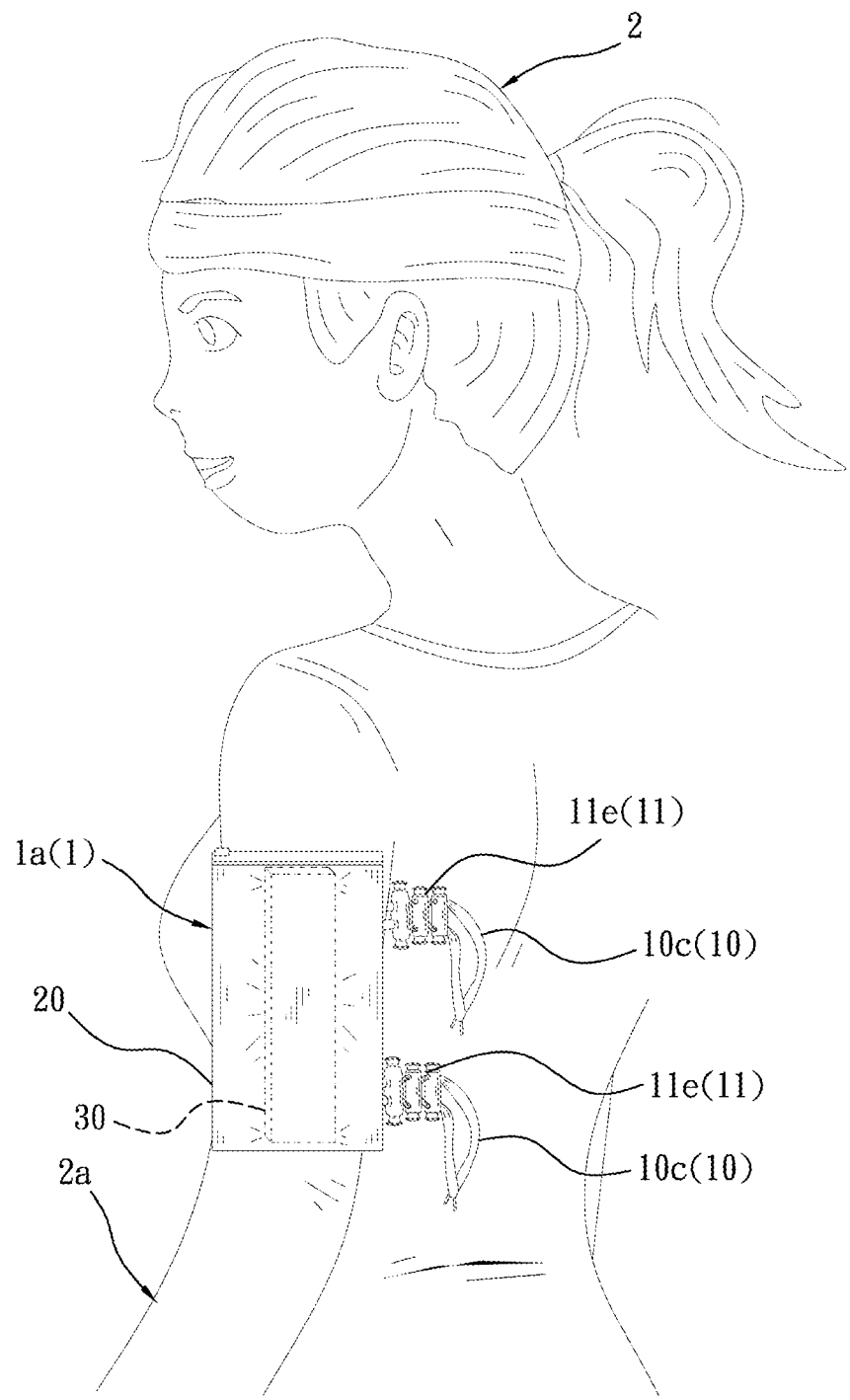
FIG. 12 is a schematic drawing showing an embodiment in a limb-carrying mode being worn on an arm of a human body according to the present invention.

The long tie 10 can be, but not limited to, a belt 10b (as shown in FIG. 6 and FIG. 7) or an elastic cord 10c (as shown in FIG. 1-5). The first connecting member 11 of the long tie 10 can be, but not limited to, double buckle type 11a (as shown in FIG. 6 and FIG. 7), quick-release buckle type 11b (as shown in FIG. 8 and FIG. 9), hook and loop type 11c (as shown in FIG. 11), snap-fastener type 11d (as shown in FIG. 10), or double hole cord lock type 11e (as shown in FIG. 1-5).

Figure 24:
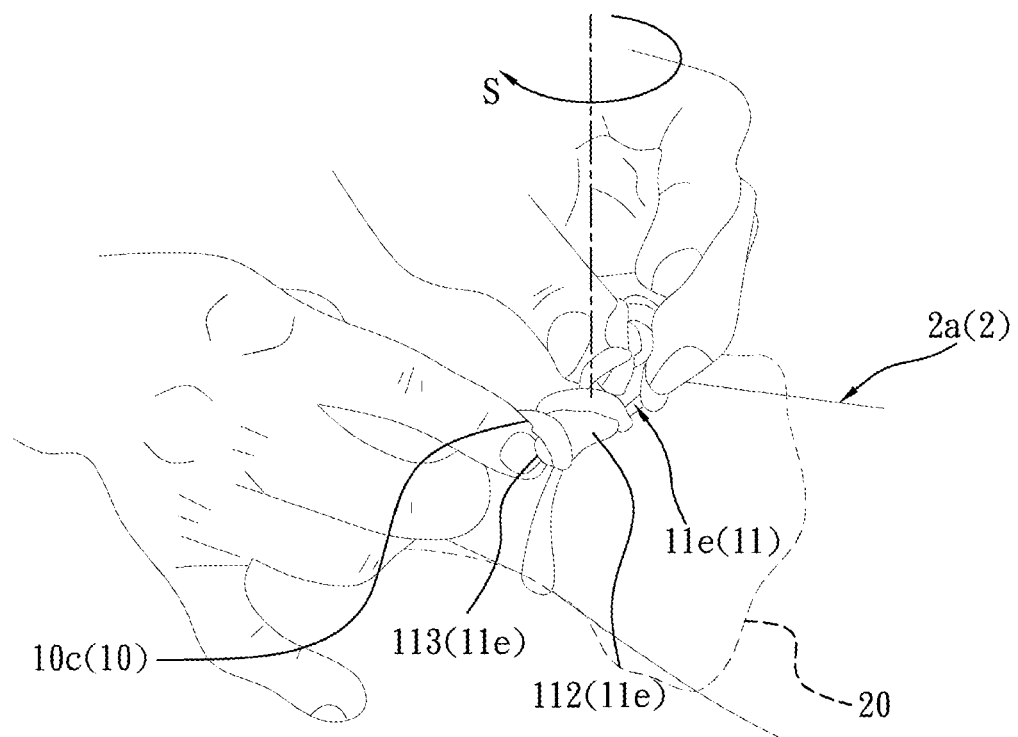
FIG. 24 is a schematic drawing showing a long tie is wound around a first connecting member in a form of double hole cord lock and then tightened after being fit on a human body according to the present invention.
Figure 25:
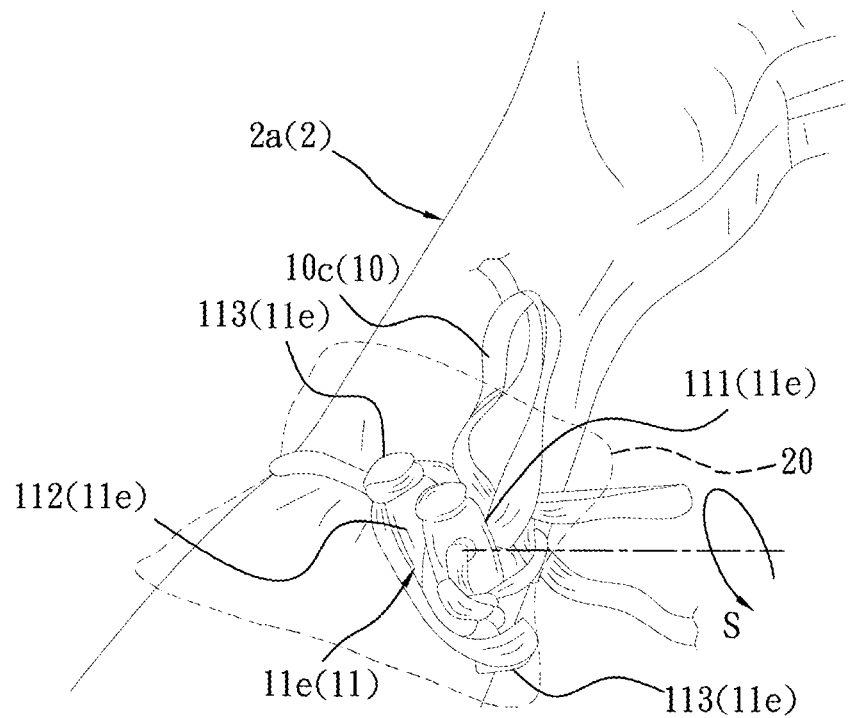
FIG. 25 is a schematic drawing showing the long tie in the embodiment of FIG. 24 tied in a slipknot after being tightened and wound according to the present invention.

When the first connecting member 11 is the double hole cord lock type 11e, the first connecting member 11 further includes at least a pair of double hole cord locks 111 and a long positioning member 112, but not limited. Refer to FIG. 24 and FIG. 25, each of two ends of both the respective double hole cord locks 111 and the long positioning member 112 is provided with a cord-wound portion 113 to which the long tie 10 (elastic cord 10c) is wound, as shown in FIG. 24).

Figure 13:
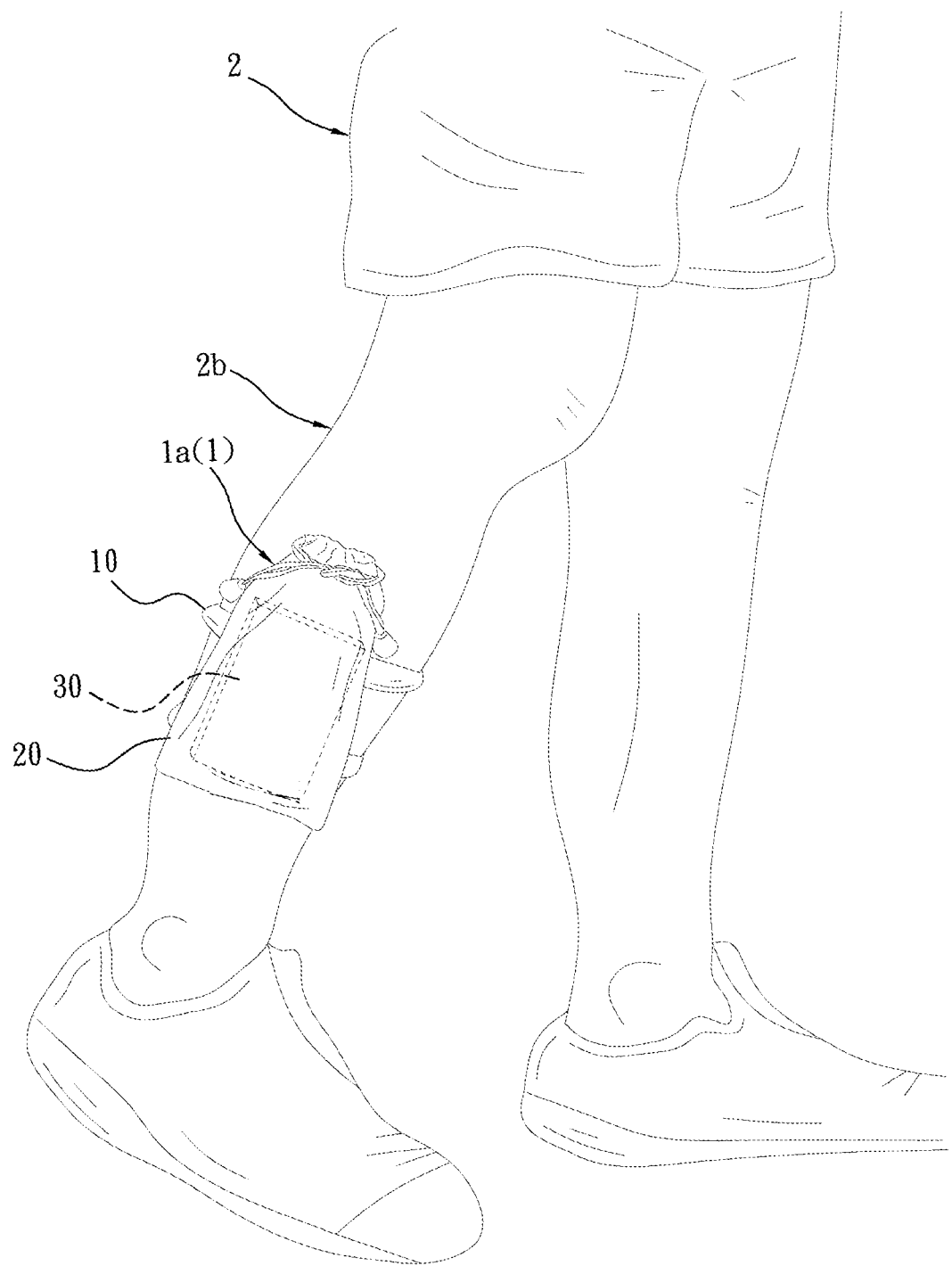
FIG. 13 is a schematic drawing showing an embodiment in a limb-carrying mode being worn on a leg of a human body according to the present invention.
Figure 20:
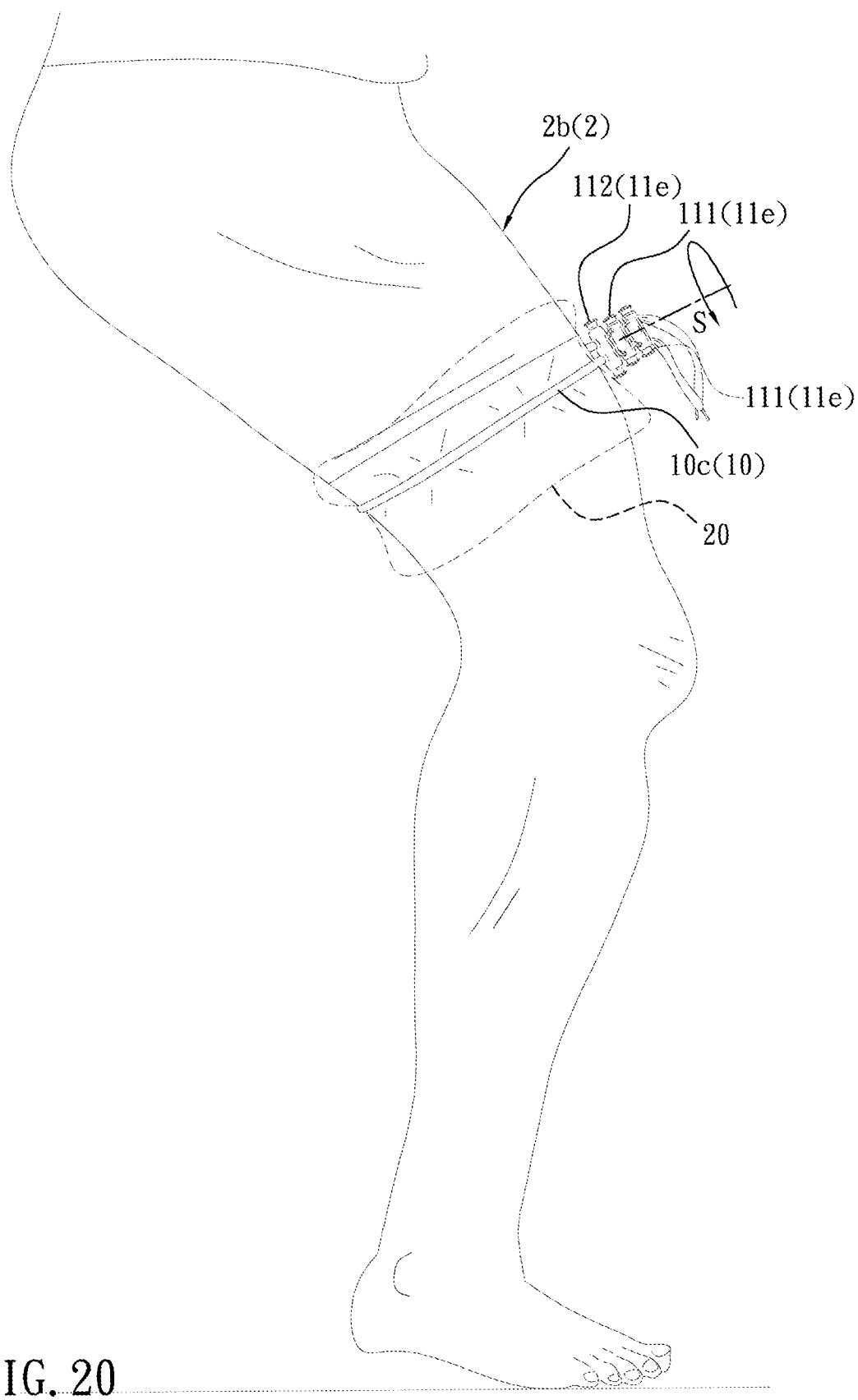
FIG. 20 is a schematic drawing showing an embodiment in which a long tie is an elastic cord worn on a leg of a human body for hemostasis according to the present invention.
Figure 21:
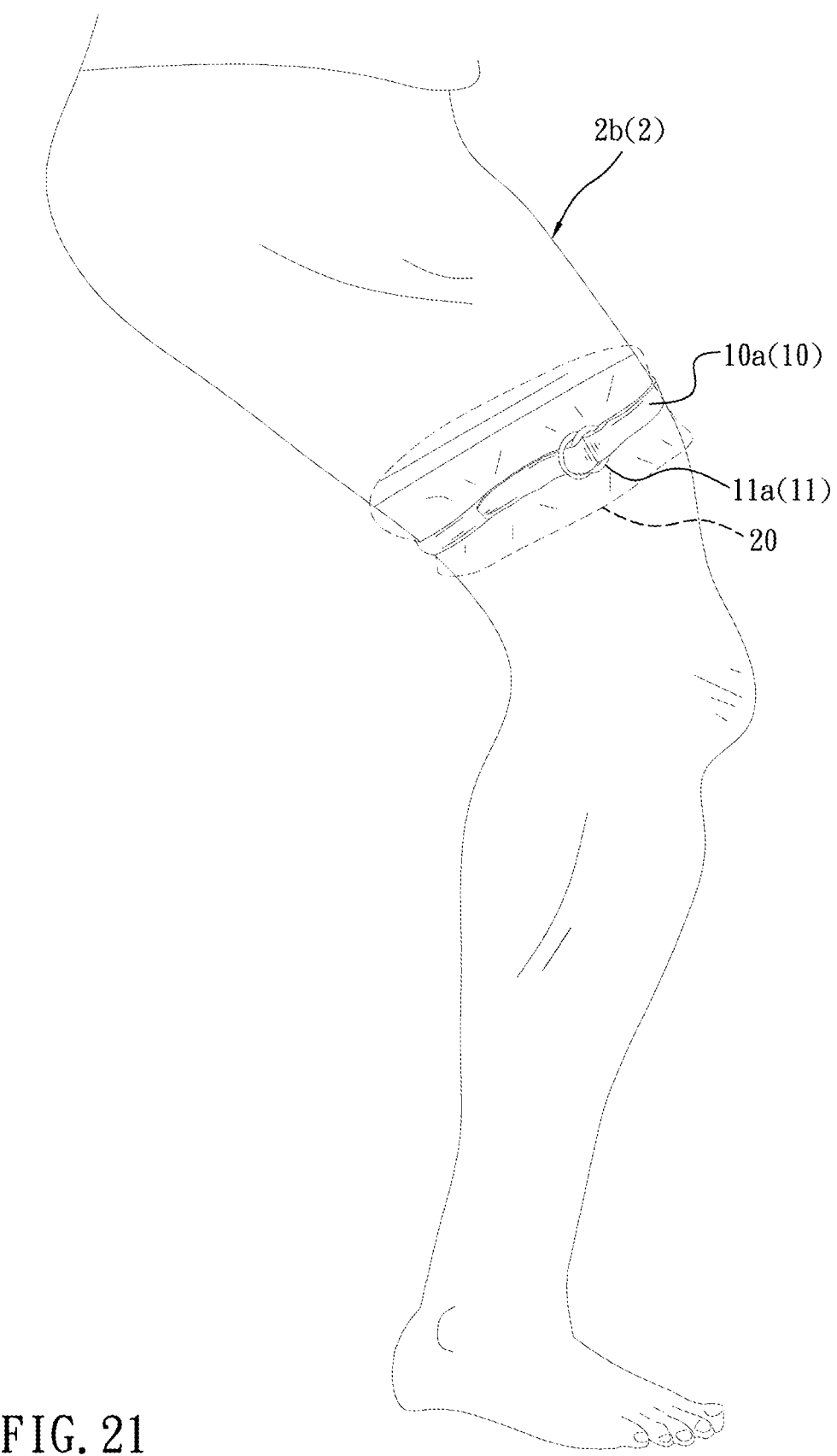
FIG. 21 is a schematic drawing showing an embodiment in which a long tie is a belt worn on a leg of a human body to stop bleeding according to the present invention.

The two long ties 10 are tightened around an arm 2a (as shown in FIG. 12 and FIG. 16-19) or a leg 2b (as shown in FIG. 13, FIG. 20, and FIG. 21) of the human body 2 and arranged adjacent to each other. Then the pouch 20 is connected to the first connecting member 11 by the second connecting member 24 so that the pouch 20 and the two long ties 10 are connected. Next the pill box 30 is mounted into the mounting space 22 of the pouch 20 to form a limb-carrying mode 1a of the multifunctional pill box carrying pouch 1, as shown in FIG. 12, FIG. 13 and FIG. 16-21.

Figure 14:
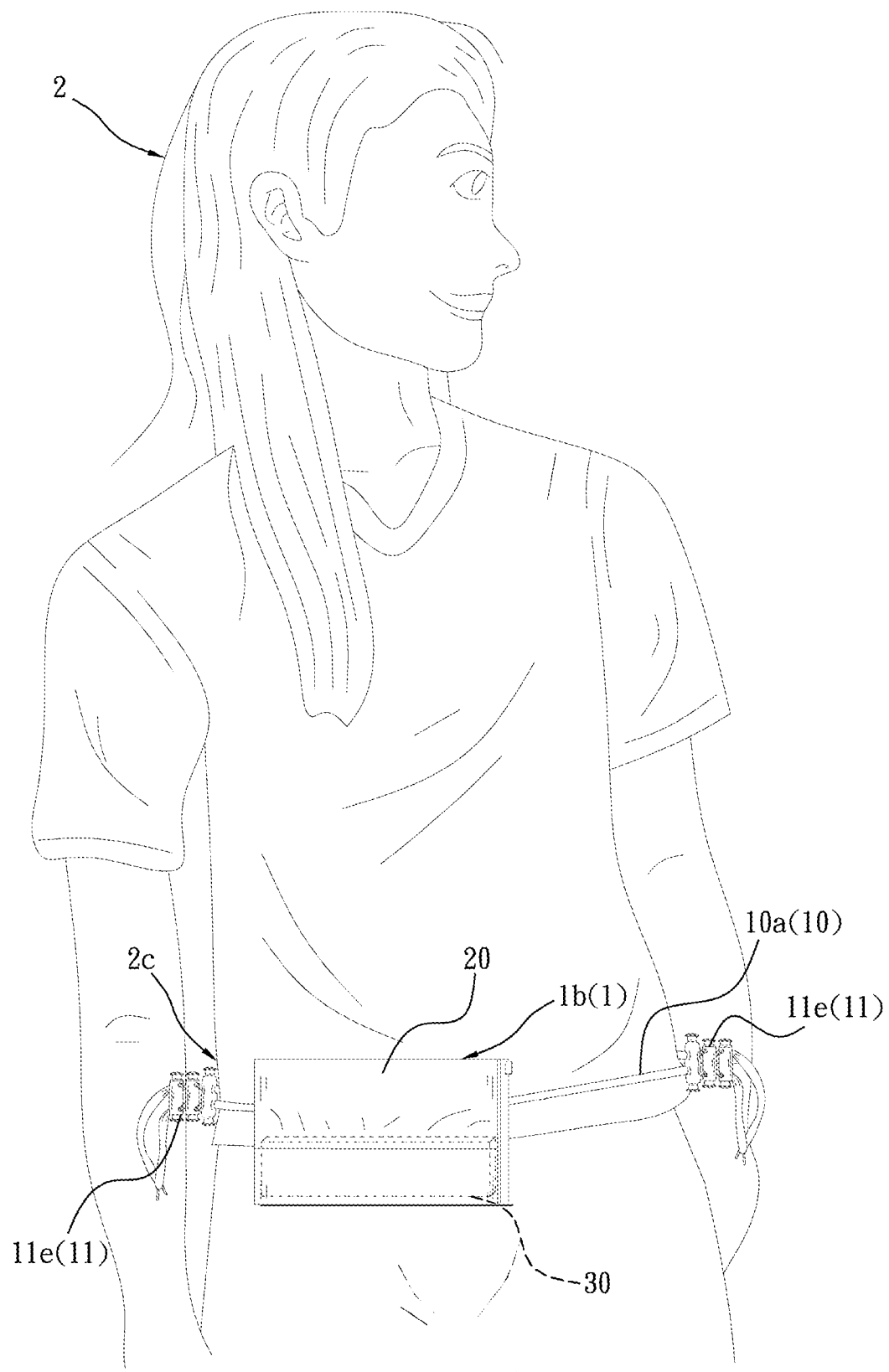
FIG. 14 is a schematic drawing showing an embodiment in a waist-carrying mode (with one pouch) being worn on a waist of a human body according to the present invention.
Figure 15:
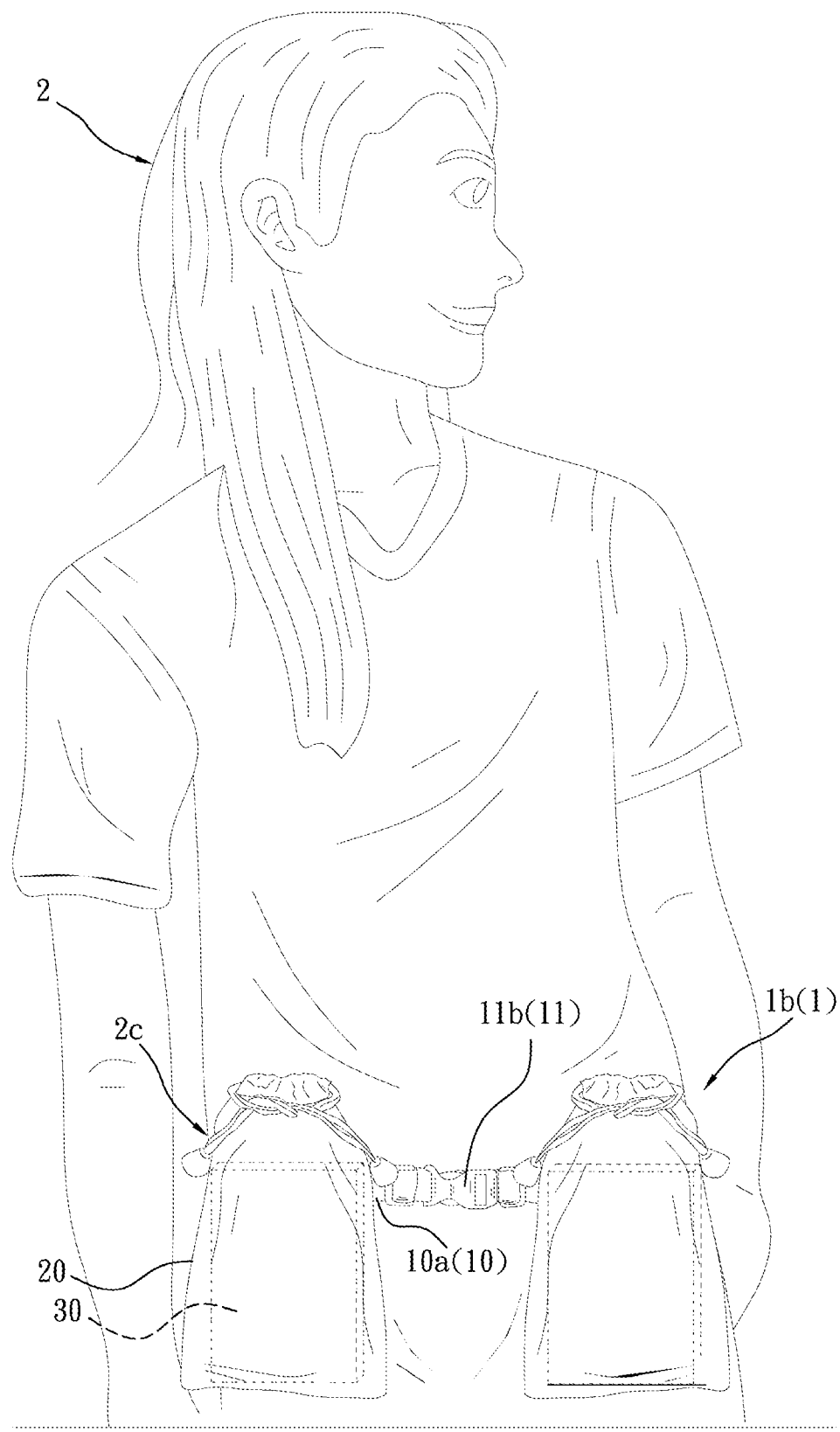
FIG. 15 is a schematic drawing showing an embodiment in a waist-carrying mode (with two pouches) being worn on a waist of a human body according to the present invention.

When the two long ties 10 form the single longer tie 10a (as shown in FIG. 3, FIG. 4, FIG. 8 and FIG. 9), the single longer tie 10a is tightened around a waist 2c of the human body 2, as shown in FIG. 14 and FIG. 15. Then the pouch 20 is connected to the first connecting member 11 by the second connecting member 24 so that the pouch 20 and the single longer tie 10a are connected. Next the pill box 30 is mounted into the mounting space 22 of the pouch 20 to form a waist-carrying mode 1b of the multifunctional pill box carrying pouch 1, as shown in FIG. 14 and FIG. 15.

Figure 16:
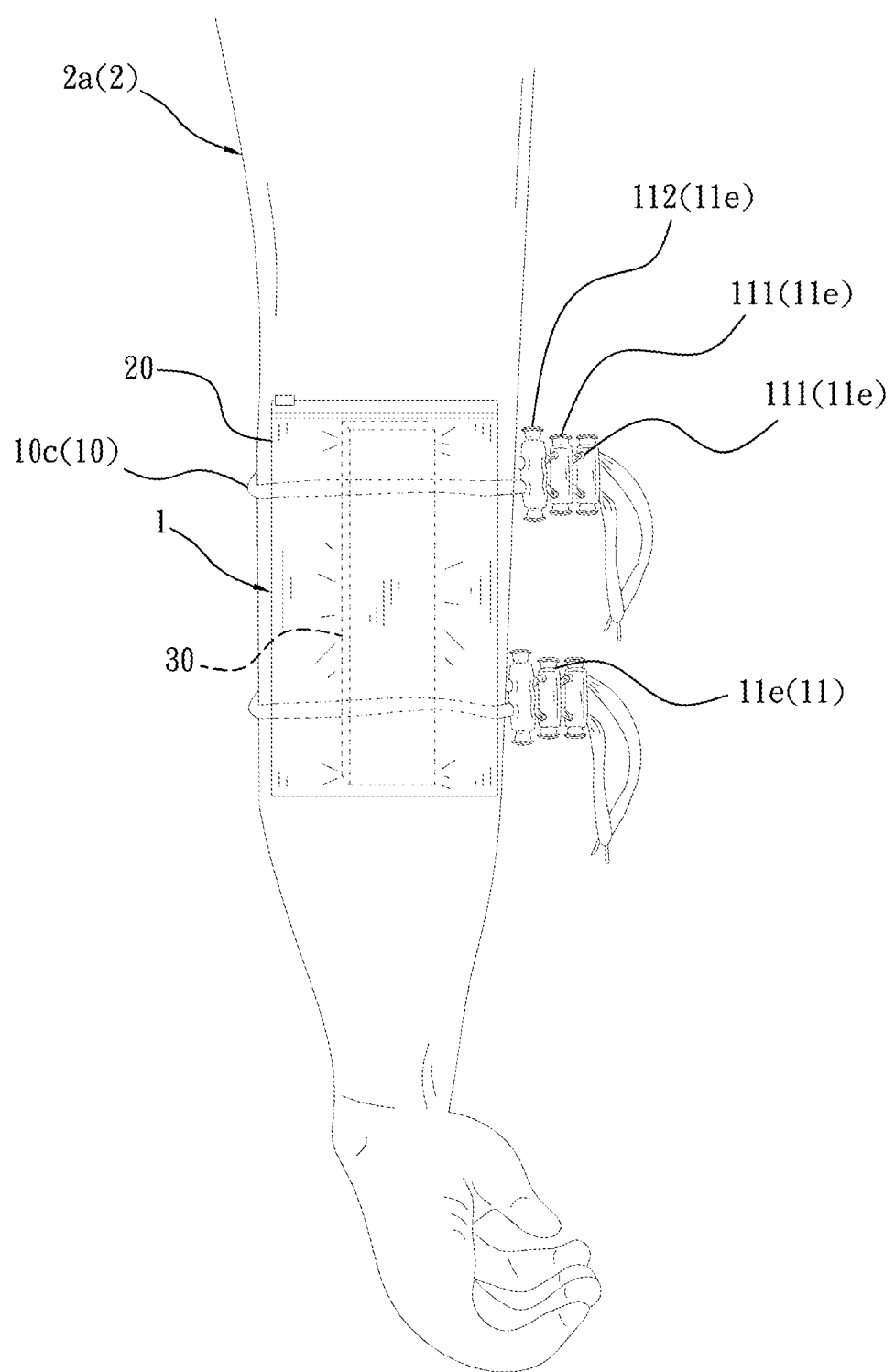
FIG. 16 is a schematic drawing showing an embodiment (with one pouch) worn on an arm of a human body for support according to the present invention.
Figure 17:
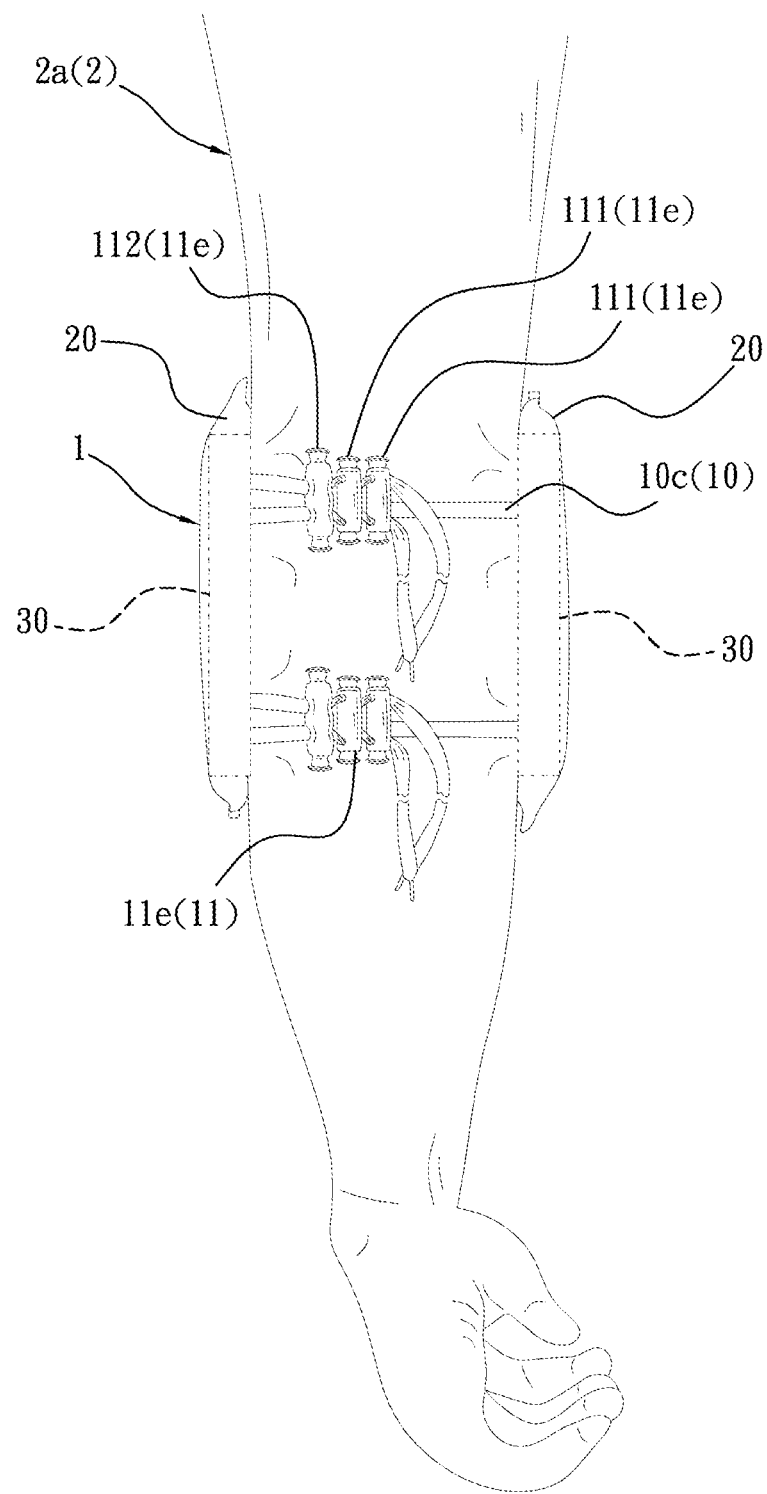
FIG. 17 is a schematic drawing showing an embodiment (with two pouches) worn on an arm of a human body for support according to the present invention.

When user's limb is injured (such as bone fracture or joint injury) and a temporary support for the limb or for hemostasis is required, the user can select the limb-carrying mode 1a of the outdoor pill box carrying pouch 1. By the at least two long ties 10 arranged adjacent to each other and tighten around the arm 2a (as shown in FIG. 16 and FIG. 17) or the leg 2b (not shown in figures) of the human body 2, the pouch 20 provided with at least one pill box 30 is attached closely to wound area 2d on the user's limb for providing support to the wound area 2d (as shown in FIG. 16 and FIG. 17) or to stop bleeding (certain area of the human body 2 such as the neck should not be tightened so tight that suffocation may occur).

Figure 26:
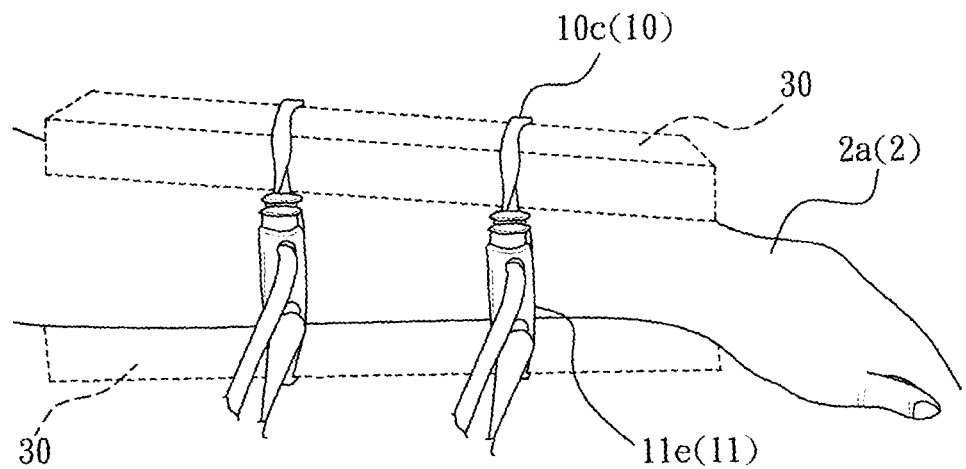
FIG. 26 is a schematic drawing showing long ties which are elastic cords are tightened around an arm of a human body for support according to the present invention.
Figure 27:
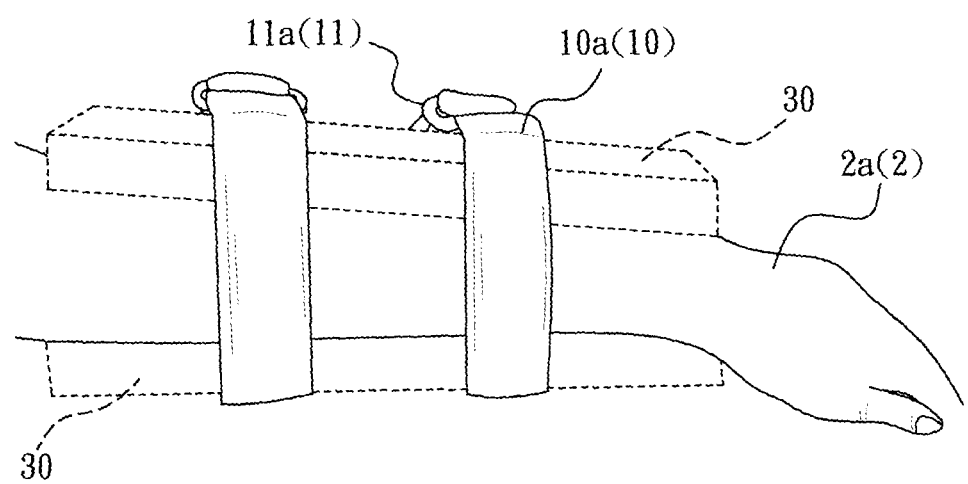
FIG. 27 is a schematic drawing showing another embodiment around an arm of a human body for supporting according to the present invention.

As to the embodiment shown in FIG. 26 and FIG. 27, not only the pill box 30 is removed from the respective pouches 20, the respective long ties 10 are also detached from the pouch 20. Then the pill box 30 is bound to the limb (such as the arm 2a) of the human body 2 by the respective long ties 10 tightened around the limb for providing support.

Refer to FIG. 18-21, when the limb of the human body 2 is cut and bleeding, remove the pill box 30 from the pouch 20 of the outdoor pill box carrying pouch 1 and then tighten the respective long ties 10 around pressure points for bleeding to stop bleeding on the limb of the human body 2.

Figure 22:
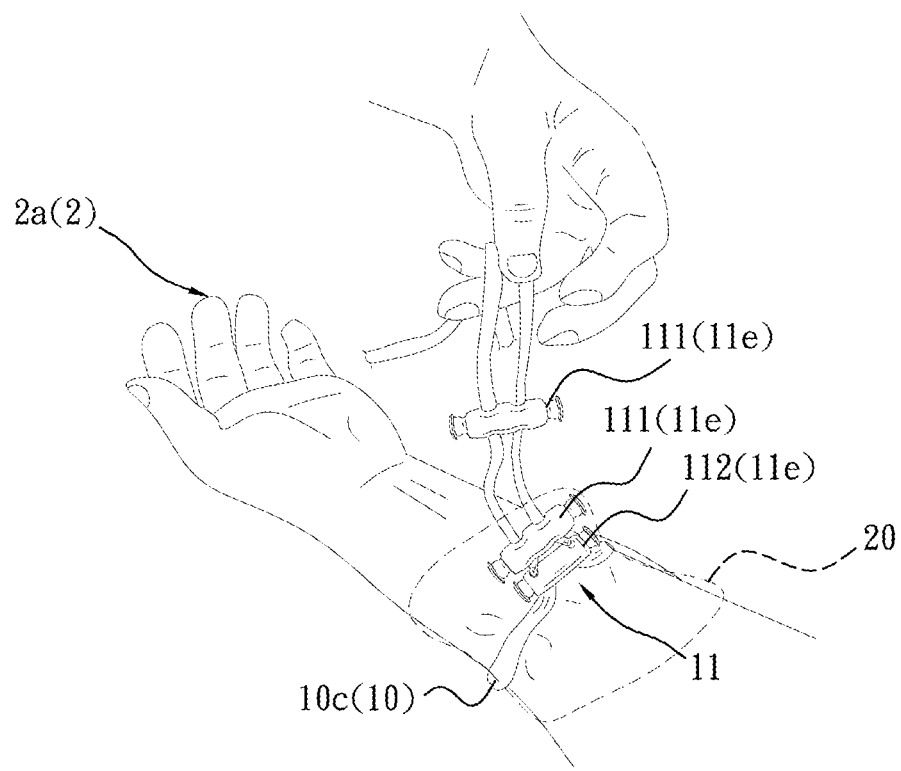
FIG. 22 is a schematic drawing showing an embodiment in which a long tie is fit on an arm of a human body according to the present invention.
Figure 23:
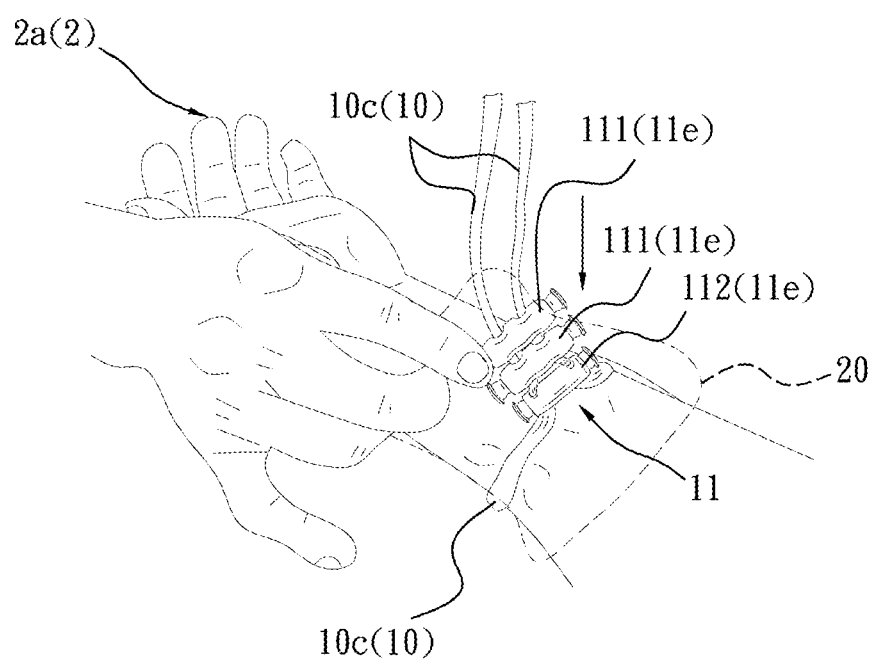
FIG. 23 is a schematic drawing showing the embodiment in FIG. 22 in which a first connecting member in a form of double hole cord lock (with two double hole cord locks) is tightened quickly according to the present invention.

Refer to the embodiment shown in FIG. 22 and FIG. 23, the long tie 10 is inserted through the respective double hole cord locks 111 and tightened quickly for hemostasis after being fit around the human body 2 when the first connecting member 11 is the double hole cord lock type 11e.

Figure 18:
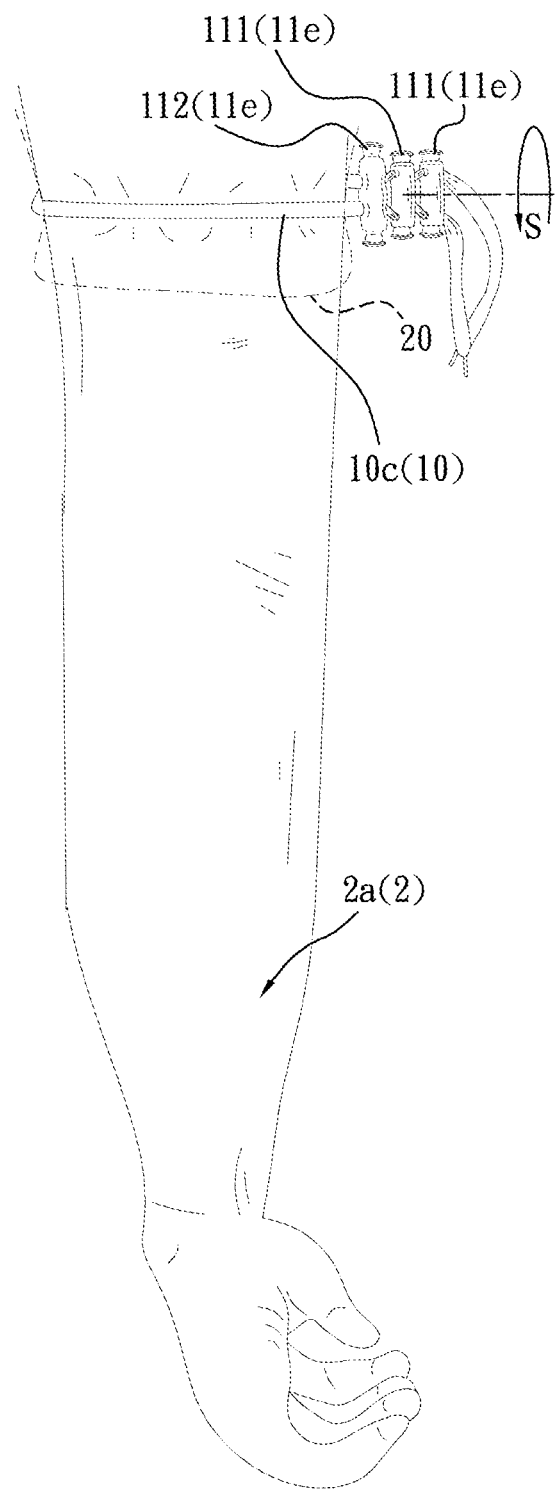
FIG. 18 is a schematic drawing showing an embodiment in which a long tie is an elastic cord worn on an arm of a human body for hemostasis according to the present invention.
Figure 19:
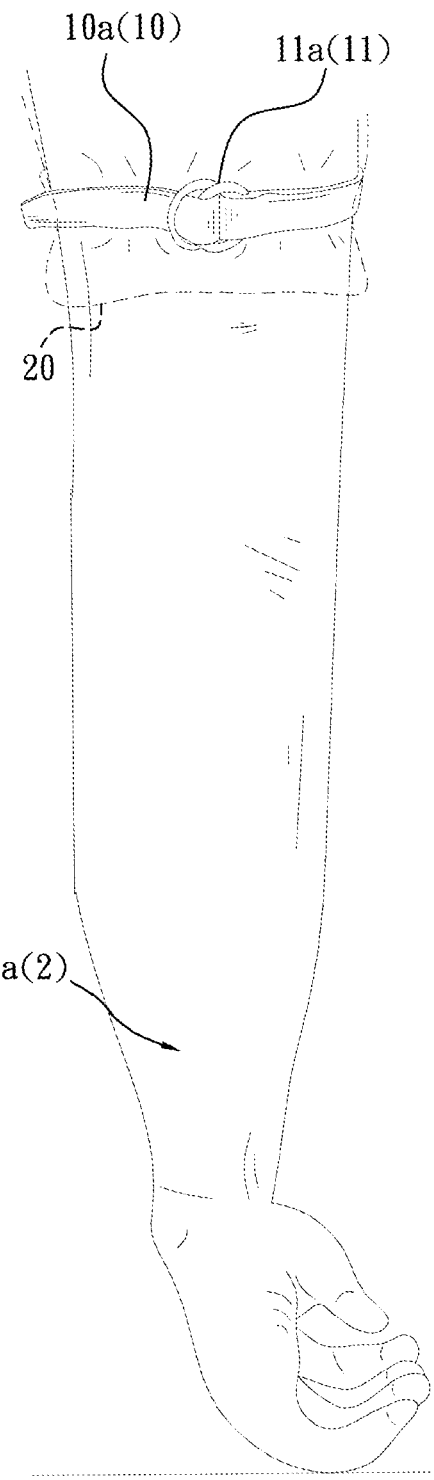
FIG. 19 is a schematic drawing showing an embodiment in which a long tie is a belt worn on an arm of a human body to stop bleeding according to the present invention.

Refer to the embodiment in FIG. 24 and FIG. 25, after the long tie 10 being tightened around the human body 2 by the double hole cord lock 111 quickly, the long tie 10 is wound around the cord-wound portions 113 on the two ends of both the double hole cord lock 111 and the long positioning member 112 and then tied in a slipknot to increase the strength of the long ties 10 being tightened for better hemostasis. Moreover, after being tightened on the human body 2, the long tie 10 is first fixed by the long positioning member 112 and then tightened again fast and rotated by the double hole cord lock 111 adjacent to the long positioning member 112 (as the arrow S in FIG. 18, FIG. 20, FIG. 24 and FIG. 25 indicates) for increasing fastening strength of the long tie 10 and further improving hemostasis. Lastly the long tie 10 is wound around the cord-wound portions 113 on the two ends of both the double hole cord lock 111 and the long positioning member 112 and then tied in a slipknot for fixing, as shown in FIG. 25. Or as shown in FIG. 18 and FIG. 20, one more double hole cord lock 111 is used for fixing and the tightening strength of the long tie 10 used to stop bleeding is further enhanced.

Once the long tie 10 is provided with two double hole cord locks 111, the long tie 10 is first fixed by the long positioning member 112 after being tightened around the human body 2 and then tightened again fast and rotated (as the arrow S in FIG. 24 indicates) by the double hole cord locks 111 to increase tightening strength of the long tie 10 for better hemostasis. At last, the long tie 10 is wound around the cord-wound portions 113 on the two ends of both the double hole cord locks 111 and the long positioning member 112 and then tied in a slipknot for fixing. Or one more double hole cord lock 111 is used for fixing so as to enhance the tightening strength of the long tie 10 for hemostasis.

Compared with the pill boxes available now, the multi-functional pill box carrying pouch 1 according to the present invention has the following advantages.
(1) The outdoor pill box carrying pouch 1 can be in either the limb-carrying mode 1a or the waist-carrying mode 1b and users can directly carry the outdoor pill box carrying pouch 1 with them without any other additional bags. The product is more convenient to carry.
(2) When the user's limb is injured and a temporary support or hemostasis is required, the user can select the outdoor pill box carrying pouch 1 to be in the limb-carrying mode 1a. By the at least two long ties 10 arranged adjacent to each other and tightened around the arm 2a or the leg 2b of the human body 1, the at least one pouch 20 with the at least one pill box 30 is attached to the wound area 2d on the user's limb closely for providing support, protection, or hemostasis to the wound area 2d. The competitiveness of the present product in the market is also increased.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalent.

The invention claimed is:

1. A multifunctional pill box carrying pouch comprising: at least one pill box which is a rigid rectangular box; at least one pouch which includes an opening, a mounting space for mounting the pill box therein, a closure portion used for closing the opening to make the mounting space in a closed state, and at least two second connecting members; and at least two long ties each of which is tightened around a human body and provided with double hole cord lock; wherein the two long ties are connected by the double cord locks to form a single longer tie; wherein the long ties are detachably connected to the pouch by the two second connecting members; wherein the two long ties are arranged adjacent to teach other and tightened around an arm or a leg of the human body; with the pill box placed in the mounting space of the pouch, thereby the multifunctional pill box carrying pouch is in a limb-carrying mode; wherein when the two long ties form the single longer tie, the single longer tie is tightened around a waist of the human body; with the pill box mounted in the mounting space of the pouch, thereby the multifunctional pill box carrying pouch is in a waist-carrying mode; wherein the limb-carrying mode of the pill box pouch is selected when the limb is injured and a temporary support is required for support or hemostasis; by the two long ties arranged adjacently and tightened around the arm or the leg of the human body, the pouch with the pill box mounted therein is closely attached to wound area on the limb for support or hemostasis.

2. The multifunctional pill box carrying pouch as claimed in claim 1, further comprising a long positioning member; wherein a cord-wound portion is disposed on each of two ends of both the double hole cord locks and the long positioning member.

3. The multifunctional pill box carrying pouch as claimed in claim 1, wherein the long tie is an elastic cord.

4. The multifunctional pill box carrying pouch as claimed in claim 1, wherein the second connecting member is selected from the group consisting of a loop type and a channel type.

5. The multifunctional pill box carrying pouch as claimed in claim 1, wherein a material for the pouch is polyethylene (PE).

6. The multifunctional pill box carrying pouch as claimed in claim 1, wherein the pill box includes a main body provided with a plurality of grids therein and a cover covering the main body so that each of the grids becomes a closed space for storage of pills.

7. The multifunctional pill box carrying pouch as claimed in claim 1, wherein a shape of the pill box is selected from the group consisting of a long strip and a wide rectangle.

8. The multifunctional pill box carrying pouch as claimed in claim 1, wherein the closure portion is selected from the group consisting of a slider and a drawstring.

9. The multi-functional pill box carrying pouch as claimed in claim 1, wherein the mounting space of the pouch is able to mount an object selected from the group consisting of a mobile phone, a water bottle and a small first aid kit.

* * * * *